United States Patent [19]

Mark

[11] Patent Number: 4,552,704
[45] Date of Patent: Nov. 12, 1985

[54] PROCESS FOR THE PRODUCTION OF AROMATIC CARBONATES

[75] Inventor: Victor Mark, Evansville, Ind.

[73] Assignee: General Electric Company, Mt. Vernon, Ind.

[21] Appl. No.: 565,896

[22] Filed: Dec. 27, 1983

[51] Int. Cl.$^4$ ............................................. C07C 68/06
[52] U.S. Cl. .................................................... 260/463
[58] Field of Search ........................................ 260/463

[56] References Cited

U.S. PATENT DOCUMENTS

| | | | |
|---|---|---|---|
| 4,263,446 | 4/1981 | Wheeler et al. | 560/75 |
| 4,281,101 | 7/1981 | Schreckenberg et al. | 528/196 |

*Primary Examiner*—Donald G. Daus
*Assistant Examiner*—Stephen M. Kapner
*Attorney, Agent, or Firm*—Myron B. Kapustij; Martin B. Barancik

[57] ABSTRACT

An improved process for the preparation of aromatic carbonates selected from aliphatic aromatic carbonates, diaromatic carbonates, and mixtures thereof comprising reacting at least one phenolic compound with at least one dialiphatic carbonate or at least one aliphatic aromatic carbonate in the presence of a catalytic amount of at least one transesterification catalyst represented by the general formula

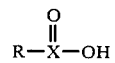

wherein:
X is selected from Sn and Ti; and
R is selected from monovalent hydrocarbon radicals and monovalent hydrocarbonoxy radicals.

18 Claims, No Drawings

PROCESS FOR THE PRODUCTION OF AROMATIC CARBONATES

BACKGROUND OF THE INVENTION

Organic carbonates such as the dialiphatic carbonates, aliphatic aromatic carbonates, and diaromatic carbonates are generally conventionally prepared by the reaction of phenols or alcohols with phosgene in the presence of acid binding agents such as the organic bases or inorganic bases. However, due to the toxicity of phosgene it is sometimes desirable to avoid the use of phosgene in the preparation of these organic carbonates.

Since the dialiphatic carbonates, such as the dialkyl carbonates, may be prepared from alcohols by routes other than those utilizing phosgene, i.e. catalytically from carbon monoxide and oxygen, it is possible to prepare the aliphatic aromatic carbonates and the diaromatic carbonates from these dialiphatic carbonates and phenols without using phosgene. Such phosgene free processes are described in U.S. Pat. Nos. 4,045,464 and 4,182,726. These patents disclose the preparation of alkyl aryl carbonates and diaryl carbonates from dialkyl carbonates and phenols in the presence of a catalyst which is selected from Lewis acids.

It would, however, be most advantageous if a phosgene free process which is more efficient than those presently available could be provided for the preparation of aliphatic aromatic and diaromatic carbonates from dialiphatic carbonates. It is, therefore, an object of the instant invention to provide such a phosgene free process for the preparation of aliphatic aromatic carbonates and diaromatic carbonates.

SUMMARY OF THE INVENTION

The instant invention is directed to a transesterification process for the preparation of aliphatic aromatic carbonates and diaromatic carbonates from dialiphatic carbonates utilizing a catalytic amount of a catalyst which is a compound represented by the general formula $$\underset{R-X-OH}{\overset{O}{\overset{\|}{}}}$$

wherein:

X is selected from Sn and Ti; and

R is selected from monovalent hydrocarbon radicals and monovalent hydrocarbonoxy radicals.

DESCRIPTION OF THE INVENTION

The instant invention is directed to an improved transesterification process for the preparation of aromatic carbonates from dialiphatic carbonates, the improvement comprising carrying out the reaction in the presence of a catalyst which is a compound represented by the general formula

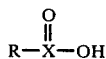

I.

wherein:

X is selected from tetravalent Sn and tetravalent Ti; and

R is selected from monovalent hydrocarbon radicals and monovalent hydrocarbonoxy radicals.

The hydrocarbon radicals represented by R are selected from the monovalent aliphatic hydrocarbon radicals and the monovalent aromatic hydrocarbon radicals. These monovalent aliphatic hydrocarbon radicals and monovalent aromatic hydrocarbon radicals include the alkyl radicals, the cycloalkyl radicals, the aryl radicals, the aralkyl radicals, and the alkaryl radicals.

The preferred alkyl radicals are those containing from 1 to about 12 carbon atoms. These include the straight chain alkyl radicals and the branched alkyl radicals. Some illustrative non-limiting examples of these alkyl radicals include methyl, ethyl, propyl, isopropyl, butyl, tertiarybutyl, pentyl, neopentyl, hexyl, and heptyl.

The preferred aryl radicals represented by R are those containing from 6 to 12 carbon atoms, and include phenyl, naphthyl, and biphenyl.

The preferred cycloalkyl radicals represented by R are those containing from 4 to about 7 ring carbon atoms. These include, but are not limited to, cyclobutyl, cyclopentyl, methycyclohexyl, cyclohexyl, and cycloheptyl.

The preferred alkaryl and aralkyl radicals represented by R are those containing from 7 to about 14 carbon atoms.

The monovalent hydrocarbonoxy radicals represented by R are selected from alkoxy radicals and aryloxy radicals. The preferred alkoxy radicals are those containing from 1 to about 12 carbon atoms. Some illustrative non-limiting examples of the alkoxy radicals include methoxy, ethoxy, propoxy, isopropoxy and butoxy. The preferred aryloxy radicals are those containing from 6 to 12 carbon atoms and include phenoxy, biphenyloxy, and naphthoxy.

The preferred compounds of Formula I are those wherein R is selected from monovalent hydrocarbon radicals.

Some illustrative non-limiting examples of the catalytic compounds of Formula I include butyltin oxide hydroxide, methyltin oxide hydroxide, phenyltin oxide hydroxide, methyltitanium oxide hydroxide, propyltitanium oxide hydroxide, benzyltin oxide hydroxide, and butyltitanium oxide hydroxide.

The aromatic carbonates which may be prepared by the process of the instant invention include the aliphatic aromatic carbonates and the diaromatic carbonates. The aliphatic aromatic carbonates may be represented by the general formula

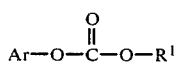

II.

wherein:

R is selected from monovalent aliphatic hydrocarbon radicals; and

Ar is selected from monovalent aromatic radicals.

The preferred monovalent hydrocarbon radicals represented by $R^1$ are the alkyl radicals and the cycloalkyl radicals. The preferred alkyl radicals are those containing from 1 to about 12 carbon atoms. These alkyl radicals include the straight chain alkyl radicals and the branched alkyl radicals. Some illustrative non-limiting examples of these alkyl radicals include methyl, ethyl, propyl, isopropyl, butyl, tertiarybutyl, pentyl, neopentyl, and hexyl. The preferred cycloalkyl radicals are those containing from 4 to about 7 ring carbon atoms.

More preferably, $R^1$ is selected from lower alkyl radicals, preferably those containing from 1 to about 4 carbon atoms. The monovalent aromatic radicals represented by Ar include those containing from 6 to 12 carbon atoms. These include phenyl, biphenyl, and naphthyl. Preferred aryl radicals represented by Ar are those represented by the general formula

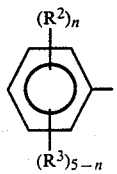

wherein:

$R^2$ is independently selected from monovalent hydrocarbon radicals and halogen radicals;

$R^3$ is hydrogen; and n is a positive integer having a value of from 0 to 5 inclusive.

The monovalent hydrocarbon radicals represented by $R^2$ include the alkyl radicals, cycloalkyl radicals, aryl radicals, aralkyl radicals, and alkaryl radicals. The preferred alkyl radicals are those containing from 1 to about 10 carbon atoms. These include the straight chain alkyl radicals and the branched alkyl radicals. The preferred cycloalkyl radicals represented by $R^2$ are those containing from 4 to about 7 ring carbon atoms. The preferred aryl radicals are those containing from 6 to 12 carbon atoms and include phenyl, naphthyl, and biphenyl. The preferred aralkyl and alkaryl radicals represented by $R^2$ are those containing from 7 to about 14 carbon atoms.

The preferred halogen radicals represented by $R^2$ are chlorine and bromine.

The diaromatic carbonates may be represented by the general formula

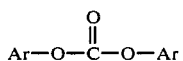    III.

wherein Ar is as defined hereinafore.

The aliphatic aromatic carbonates of the instant invention may be prepared by the reaction, in the presence of a catalytic amount of the catalyst of Formula I, of at least one dialiphatic carbonate with at least one phenol. The dialiphatic reactant may be represented by the general formula

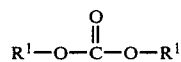

wherein $R^1$ is as defined hereinafore. It is to be understood that both $R^1$s may be the same, or they may be different. The phenol reactant may be represented by the general formula

wherein Ar is as defined hereinafore.

The reaction of the phenol with the dialiphatic carbonate may be represented by the formula

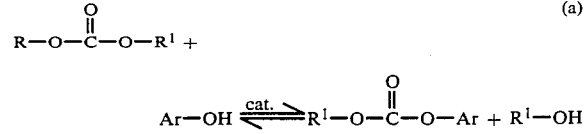

wherein $R^1$ and Ar are as defined hereinafore and cat. is a catalytic amount of the catalyst of the instant invention.

The diaromatic carbonates of the instant invention may be prepared by either one of two methods. The first method involves the reaction of the aliphatic aromatic carbonate formed as described hereinafore with a phenol in the presence of a catalytic amount of the catalyst of the instant invention. This reaction may be represented by the general formula

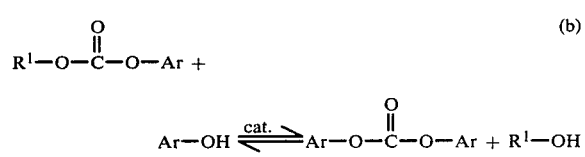

wherein Ar, $R^1$ and cat. are as defined hereinafore.

The second method involves the reaction of the aliphatic aromatic carbonate with itself or with another aliphatic aromatic carbonate in the presence of a catalytic amount of the catalyst of the instant invention. This reaction may be represented by the general formula

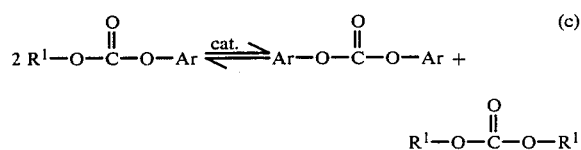

wherein Ar, $R^1$ and cat. are as defined hereinafore.

The reactions depicted by formulae (a), (b) and (c) may be carried out in the liquid phase, with or without the presence of a solvent, at temperatures of from about 60° C. to about 300° C., preferably from about 150° C. to about 250° C. These reactions may be carried out at pressures ranging from subatmospheric pressures to superatmospheric pressures, e.g. from about 0.1 to about 50 atmospheres. These reactions proceed readily at atmospheric pressure.

Since the reactions depicted in Formulae (a) and (b) are equilibrium reactions, it is advantageous to remove the alcohol formed so as to continuously shift the equilibrium until the reactions reach completion. Since the alcohol byproduct is most conveniently removed by distillation it is desirable that the reactants in the equations depicted by Formulae (a) and (b) are so selected that the $R^1$—OH byproduct has a lower boiling point than the Ar—OH reactant and thus can be distilled off as it is formed. It is for this reason that the lower dialiphatic carbonates or aliphatic aromatic carbonates are the preferred reactants in the processes of the instant invention, i.e., $R^1$ is a lower alkyl radical containing from 1 to about 4 carbon atoms in the aliphatic aromatic carbonates and the dialiphatic carbonates described hereinafore.

The preparation of the diaromatic carbonates by the reaction depicted in Formula (c) may also be conveniently achieved by the distillation of the dialiphatic carbonate coproduct. For this reason, it is also preferred that the aliphatic aromatic carbonate reactant be a lower aliphatic aromatic carbonate so that the dialiphatic carbonate coproduct may be readily distilled off, i.e., $R^1$ in the aliphatic aromatic carbonate is a lower alkyl radical containing from 1 to about 4 carbon atoms.

In the preparation of the diaromatic carbonates of the instant invention it is preferred that the reaction process be continuous and be carried out in the same reaction vessel. That is to say, once the aliphatic aromatic carbonate is formed by the reaction of the dialiphatic carbonate and the phenol it is not removed from the reaction vessel but is allowed to further react with the phenol to form the diaromatic carbonate.

While theoretically it requires two moles of phenol for every mole of dialiphatic carbonate to produce the diaromatic carbonate, in practice it is generally preferred to use an excess of the phenol reactant. Thus, for example, it is generally preferred to utilize an excess of phenol when reacting the dialiphatic carbonate with the phenol to form the aliphatic aromatic carbonate, and it is also preferred that an excess of phenol be present during the subsequent reaction of the aliphatic aromatic carbonate with the phenol to form the diaromatic carbonate. Since it is generally preferred to employ a continuous process for the preparation of the diaromatic carbonates from the dialiphatic carbonates, generally it is preferred to use more than two moles of phenol for every mole of dialiphatic carbonate reactant utilized.

The amount of the catalyst of the instant invention utilized in the exchange reactions of this invention is a catalytic amount. By catalytic amount is meant an amount effective to catalyze the transesterification reaction for the preparation of the aliphatic aromatic carbonates from the dialiphatic carbonates and the phenols and the diaromatic carbonates from the aliphatic aromatic carbonates and the phenols. Generally, this amount is in the range of from about 0.01 to about 25 weight percent, based on the amounts of dialiphatic carbonate or aliphatic aromatic carbonate reactants employed, and preferably from about 0.1 to about 20 weight percent.

While not wishing to be bound by any theory, it is believed that the catalysts of the instant invention exhibit improved catalytic activity because they are hybrids of Lewis acids and protic acids. That is to say, the catalysts of Formula I exhibit the properties of Lewis acids in that they may function as electron pair acceptors and the properties of protic acids in that they may function as proton donors.

It is further contemplated that the instant catalyst of Formula I would be effective in catalyzing any transesterification reaction. Thus, while the instant disclosure and examples are directed to the formation of aliphatic aromatic carbonates and diaromatic carbonates from dialiphatic carbonates and aliphatic aromatic carbonates, respectively, it is contemplated that this catalyst would be effective in the formation of other esters, particularly other aromatic esters, via a transesterification process.

DESCRIPTION OF THE PREFERRED EMBODIMENT

In order to more fully and clearly illustrate the present invention the following examples are set forth. It is intended that the examples be considered as illustrative rather than limiting the invention as disclosed and claimed herein. In the examples all parts and percentages are on a weight basis, unless otherwise indicated.

The following examples illustrate the preparation of aliphatic aromatic (alkyl aryl) carbonates and diaromatic (diaryl) carbonates from dialiphatic (dialkyl) carbonates utilizing conventional Lewis acid catalysts. These examples fall outside the scope of the instant invention and are presented for comparative purposes only.

EXAMPLE 1

To a 500 milliliter 4-necked flask equipped with a mechanical stirrer, thermometer, and a one foot long column, filled with glass helices and capped by a distillation head with a thermometer and reflux condenser, are charged 188.2 grams (2.0 moles) of phenol and 4 grams of dibutyltin maleate catalyst. This mixture is heated, with stirring, to 180° C. When this temperature is reached, 29.5 grams (0.25 mole) of diethyl carbonate are added dropwise from the addition funnel. The addition of the diethyl carbonate is carried out dropwise and over a period of about one hour so as to maintain the pot temperature at or about 180° C. After the addition of the diethyl carbonate is complete, the ethyl alcohol liberated is continuously collected and the quantity collected is noted. The reaction is continued for 7 hours. At the end of the 7 hour reaction period the reaction mixture is weighed and analyzed by gas chromatography for the ethyl phenyl carbonate and the diphenyl carbonate. The results are set forth in Table I.

EXAMPLE 2

The procedure of Example 1 is substantially repeated except that the 4 grams of dibutyltin maleate catalyst are replaced with 4 grams of dibutyltin diacetate catalyst. The results are set forth in Table I.

The following example illustrates the preparation of aliphatic aromatic (alkyl aryl) carbonate and diaromatic (diaryl) carbonate from dialiphatic (dialkyl) carbonate utilizing the catalyst of the instant invention.

EXAMPLE 3

To a 500 milliliter 4-necked flask equipped with a mechanical stirrer, thermometer, and a one foot long column, filled with glass helices and capped by a distillation head with a thermometer and reflux condenser, are charged 188.2 grams (2.0 mole) of phenol and 4 grams of butyltin oxide hydroxide catalyst. This mixture is heated, with stirring, to 180° C. When this temperature is attained 29.5 grams of diethyl carbonate are added from the addition funnel. The addition of the diethyl carbonate is carried out dropwise over a period of about one hour so as to maintain the pot temperature at or about 180° C. After the addition of the diethylcarbonate is complete, the ethyl alcohol liberated is continuously collected and the quantity collected is noted. The reaction is continued for 7 hours and at the end of this reaction period the reaction mixture is weighed and analyzed by gas chromataography for the ethyl phenyl carbonate and the diphenyl carbonate. The results are set forth in Table I.

TABLE I

| Example No. | Catalyst (gms.) | Alcohol liberated (gms.) | | | alkyl aryl carbonate (mole %) 7 hrs. | diaryl carbonate (mole %) 7 hrs. |
| --- | --- | --- | --- | --- | --- | --- |
| | | 3 hrs. | 5 hrs. | 7 hrs. | | |
| 1 | 4.0 | 2.3 | 4.4 | 6.6 | 2.7 | 3.3 |
| 2 | 4.0 | 1.8 | 3.9 | 5.7 | 0.1 | 0.0 |
| 3 | 4.0 | 5.3 | 8.5 | 10.7 | 7.6 | 4.2 |

The data in Table I clearly illustrate that the process of the instant invention, i.e., one utilizing the catalyst of Formula I, is more efficient in producing the aliphatic aromatic carbonates and the diaromatic carbonates from the dialiphatic carbonates than the processes utilizing a conventional Lewis acid catalyst. Thus, a comparison of Example 3 with Examples 1 and 2 shows that the process of the instant invention results in more of the aliphatic aromatic carbonate and diaromatic carbonate being formed than does the process falling outside the scope of the instant invention.

Obviously, other modifications and variations of the present invention are possible in light of the above teachings. It is, therefore, to be understood that changes may be made in the particular embodiments of the invention described which are within the full intended scope of the invention as defined by the appended claims.

What is claimed is:

1. An improved process for preparing aromatic carbonates selected from aliphatic aromatic carbonates represented by the formula $$Ar-O-\overset{O}{\underset{\|}{C}}-O-R^1,$$

diaromatic carbonates represented by the formula $$Ar-O-\overset{O}{\underset{\|}{C}}-O-Ar,$$

wherein Ar is independently selected from monovalent aromatic radicals and R¹ is selected from monovalent aliphatic radicals, and mixtures thereof which comprises reacting a phenolic compound represented by the formula Ar—OH with a dialiphatic carbonate represented by the formula $$R^1-O-\overset{O}{\underset{\|}{C}}-O-R^1$$

or an aliphatic aromatic carbonate represented by the formula $$Ar-\overset{O}{\underset{\|}{C}}-O-R^1$$

in the presence of a catalytic amount of a transesterification catalyst, the improvement comprising utilizing as the catalyst at least one compound represented by the formula $$R-\overset{O}{\underset{\|}{X}}-OH$$

wherein:

X is selected from Sn and Ti; and

R is selected from monovalent hydrocarbon radicals.

2. The process of claim 1 wherein R is selected from monovalent hydrocarbon radicals.

3. The process of claim 2 wherein said monovalent hydrocarbon radicals are selected from aliphatic monovalent hydrocarbon radicals.

4. The process of claim 3 wherein said monovalent aliphatic hydrocarbon radicals are selected from alkyl radicals and cycloalkyl radicals.

5. The process of claim 2 wherein said monovalent hydrocarbon radicals are selected from monovalent aromatic hydrocarbon radicals.

6. The process of claim 5 wherein said monovalent aromatic hydrocarbon radicals are selected from aryl radicals, aralkyl radicals, and alkaryl radicals.

7. The process of claim 1 wherein R is selected from monovalent hydrocarbonoxy radicals.

8. The process of claim 7 wherein said monovalent hydrocarbonoxy radicals are selected from alkoxy radicals and aryloxy radicals.

9. The process of claim 1 wherein said catalytic amount is in the range of from about 0.01 to about 25 weight percent, based on the amounts of aliphatic aromatic or dialiphatic carbonates present.

10. The process of claim 9 wherein X is Sn.

11. The process of claim 10 wherein R is an alkyl radical.

12. The process of claim 11 wherein said alkyl radical is butyl.

13. The process of claim 1 wherein X is Ti.

14. The process of claim 13 wherein R is selected from monovalent hydrocarbon radicals.

15. The process of claim 14 wherein said monovalent hydrocarbon radicals are selected from aliphatic monovalent hydrocarbon radicals.

16. The process of claim 15 wherein said monovalent aliphatic hydrocarbon radicals are selected from alkyl radicals and cycloalkyl radicals.

17. The process of claim 14 wherein said monovalent hydrocarbon radicals are selected from monovalent aromatic hydrocarbon radicals.

18. The process of claim 17 wherein said monovalent aromatic hydrocarbon radicals are selected from aryl radicals, aralkyl radicals, and alkaryl radicals.

* * * * *